United States Patent
Davidson et al.

(10) Patent No.: US 9,126,877 B2
(45) Date of Patent: Sep. 8, 2015

(54) POLYMERS OF ISOBUTENE FROM RENEWABLE SOURCES

(75) Inventors: Gregory J. E. Davidson, London (CA); Gilles Arsenault, London (CA); Thomas Foellinger, Dormagen (DE); Ralf-Ingo Schenkel, Lagenfeld (DE); Kevin Kulbaba, London (CA); Jessica Lee Watson, London (CA)

(73) Assignee: LANXESS INTERNATIONAL S.A., Granges-Paccot (CH)

( * ) Notice: Subject to any disclaimer, the term of this patent is extended or adjusted under 35 U.S.C. 154(b) by 0 days.

(21) Appl. No.: 13/876,506

(22) PCT Filed: Sep. 30, 2011

(86) PCT No.: PCT/CA2011/050616
§ 371 (c)(1),
(2), (4) Date: Nov. 6, 2013

(87) PCT Pub. No.: WO2012/040859
PCT Pub. Date: Apr. 5, 2012

(65) Prior Publication Data
US 2014/0051819 A1    Feb. 20, 2014

Related U.S. Application Data

(60) Provisional application No. 61/388,785, filed on Oct. 1, 2010, provisional application No. 61/393,541, filed on Oct. 15, 2010, provisional application No. 61/393,549, filed on Oct. 15, 2010.

(51) Int. Cl.
*C08F 10/10* (2006.01)
*C08F 110/10* (2006.01)
*C07C 7/13* (2006.01)
*C07C 7/12* (2006.01)
*C08F 2/06* (2006.01)

(52) U.S. Cl.
CPC ... *C07C 7/12* (2013.01); *C07C 7/13* (2013.01); *C08F 2/06* (2013.01); *C08F 110/10* (2013.01)

(58) Field of Classification Search
CPC .................................. C07C 7/13; C08F 10/10
USPC ........ 585/820, 800, 868; 526/348.7, 194, 226
IPC .................................................. C07C 7/13, 7/12
See application file for complete search history.

(56) References Cited

U.S. PATENT DOCUMENTS

| | | | | |
|---|---|---|---|---|
| 3,061,654 A * | 10/1962 | Genshelmer et al. | ......... | 585/820 |
| 3,151,178 A * | 9/1964 | Etherington | ................... | 585/829 |
| 3,531,539 A * | 9/1970 | Tidwell | ........................ | 585/251 |
| 6,596,909 B2 * | 7/2003 | Nishijima et al. | ............. | 568/917 |
| 8,193,402 B2 * | 6/2012 | Gruber et al. | ................. | 585/240 |
| 8,450,543 B2 * | 5/2013 | Peters et al. | .................. | 585/240 |
| 2010/0216958 A1 | 8/2010 | Peters | | |
| 2013/0261323 A1 | 10/2013 | Peters | | |

OTHER PUBLICATIONS

EP Extended Search Report dated Oct. 30, 2014 (10 pages).

* cited by examiner

*Primary Examiner* — Rip A Lee

(57) ABSTRACT

The present invention is directed to a method for preparing isobutene from a renewable source and their use in the preparation of renewable polymers. The invention also discloses purification of isobutene, selective removal of 1-butene, cis-2-butene and trans-2-butene using microporous adsorbent material, and the oligomerization of the purified liquid isobutene yielding diisobutenes and triisobutenes.

14 Claims, 5 Drawing Sheets

POLYMERS OF ISOBUTENE FROM RENEWABLE SOURCES

FIELD OF THE INVENTION

The present invention relates generally to preparation of renewable polymers, specifically to polymers obtained from renewable isobutene monomer. The invention also relates to selective separation of isobutene from an olefin mixture, and the oligomerization of the purified isobutene.

BACKGROUND OF THE INVENTION

Isobutene (also referred to as isobutylene or 2-methylpropene) is a hydrocarbon of significant industrial importance. Isobutene is used as an intermediate in the production of a variety of products. For example, it is reacted with methanol and ethanol in the manufacture of the gasoline oxygenates methyl tert-butyl ether (MTBE) and ethyl tert-butyl ether (ETBE), respectively. Alkylation with butane produces isooctane, another fuel additive. Isobutene is also used in the production of methacrolein. Antioxidants such as butylated hydroxytoluene (BHT) and butylated hydroxyanisole (BHA) are produced by Friedel-Crafts alkylation of phenols using isobutylene.

Polymerization of isobutene with isoprene produces butyl rubber, a random copolymer of isobutene and isoprene, which is well known for its excellent thermal stability, ozone resistance and desirable dampening characteristics. Currently butyl rubber is industrially produced utilizing isobutene derived from petrochemical source(s). Isobutene used in industrial applications typically is prepared as a by-product of conventional industrial dehydration processes such as, thermal cracking process in petroleum, refining the purification of which is a multistep energy intensive process. The amount of isobutene produced varies depending on the composition of the petrochemical feedstock and the type of cracking used in the process. The stream is typically characterized by a high butadiene content and low amount of butene. After separating the butadiene, the remainder of the stream contains less than 50% isobutene. The volatility of oil prices has made petro-based feedstock of isobutene unreliable while the cracking of lighter crude has seen the overall percentage of isobutene in the C4 stream drop dramatically.

As petrochemically derived isobutene is obtained from complex hydrocarbon mixtures, it is usually necessary to carry out a further extensive (and expensive) purification prior to polymerization. Multistep processes for purification are energy and resource intensive. Accordingly, processes capable of directly providing relatively pure isobutene which require little or no additional purification would be desirable.

There is increasing environmental concern that the use of petroleum-derived hydrocarbons as basic raw materials (e.g., butadiene or isoprene) contributes to environmental hazards such as global warming and pollution and fosters overdependence on unreliable petroleum supplies. These concerns increase demand for environmentally friendly processes and products. Accordingly, there is a need for a low carbon footprint solution to produce isobutene-based polymers utilizing renewable (i.e., biologically derived) sources of monomers such as isobutene and low energy chemical processes.

There is also a concern that future supplies of isobutene from petrochemical based sources will be inadequate to meet projected needs and that prices will rise to unprecedented levels. Accordingly, there is a current need to procure a source of feedstock material, such as isobutene from a low and reliable cost, renewable source which is environmentally friendly.

U.S. Application No. 12/711,919 (published as US 2010/0216958 A1) discloses use of isobutanol obtained from renewable sources in the preparation of isoprene, butadiene and isobutene. In the process disclosed therein, isobutene is separated from 1,3-butadiene using acetonitrile extraction, following a dehydrogenation (400° C., two catalyst system—$ZnFe_2O_4$ and $Co_9Fe_3BiMoO_{51}$) of the linear butenes (1-butene, cis- and trans-butene). The separation yields isobutene with residual linear butenes and trace amounts of butadiene. Linear butenes and 1,3-butadiene are known to act as potent poisons/chain transfer agents in the cationic polymerizations of butyl rubber. Parts per million (ppm) quantities could affect the molecular weight of the resultant polymer, therefore high purity isobutene feeds are required. The initiators/co-initiator used for the polymerization, particularly for preparing butyl rubber is highly sensitive to impurities.

SUMMARY OF THE INVENTION

It is an object of the present invention to provide polymers of isobutene obtained from renewable sources. In accordance with an aspect of the present invention there is provided a method of preparing a renewable polyisobutene polymer, comprising providing an olefin mixture comprising isobutene and one or more linear butenes, wherein the olefin mixture is obtained from a renewable hydrocarbon source; contacting the olefin mixture with an adsorbent microporous material having an effective pore opening of 5 Å to 5.4 Å, wherein the linear butenes are selectively adsorbed to the microporous material; isolating the isobutene from contact with the microporous material; and polymerizing the renewable isobutene to obtain the renewable polymer.

In accordance with an aspect of the present invention there is provided a polyisobutene polymer comprising isobutene units derived from a renewable hydrocarbon source and having a total biobased content greater than 0%.

In accordance with an aspect of the present invention there is provided a method of preparing high purity renewable isobutene comprising providing an olefin mixture comprising isobutene and one or more linear butenes, wherein the olefin mixture is obtained from a renewable hydrocarbon source; contacting the olefin mixture with an adsorbent microporous material having an effective pore opening of 5 Å to 5.4 Å, wherein the linear butenes are selectively adsorbed by the microporous material; and isolating the renewable isobutene from contact with the microporous material.

In accordance with an aspect of the present invention there is provided a method for preparing one or more oligomeric isoalkenes comprising contacting a reaction mixture comprising the isoalkenes with an adsorbent microporous material under conditions suitable for oligomerization of isoalkenes, the adsorbent microporous material having an effective pore size, based on critical diameter of alkenes, which preferentially adsorbs linear alkenes and excludes isoalkenes, and isolating the oligomeric isoalkenes from contact with the microporous material.

BRIEF DESCRIPTION OF THE DRAWINGS

The invention will now be described by way of reference to the drawings, in which.

DETAILED DESCRIPTION OF THE INVENTION

The present invention is directed to a simple process for obtaining high purity isobutene from bio-isobutanol, which is suitable for use in polymerization reactions.

The present invention is also directed to an improved process for preparing high molecular weight elastomeric polymers such as butyl rubber from high purity renewable isobutene feedstock obtained via a simple, and energy efficient purification process.

This invention is further directed to polymers comprising repeating units derived from high purity renewable isobutene and having a biobased content greater than 0%.

The invention also relates to selective removal of 1-butene, cis-2-butene and trans-2-butene, and the oligomerization of the purified isobutene yielding diisobutenes and diisobutenes.

The terms "renewable" or "bio-based" used herein with regard to a material or a compound (such as alcohols, alkyl, olefins, di-olefins, etc.) denote a material or compound obtained from a "new carbon" source as measured by ASTM test method designated as D 6866, "Determining the Biobased Content of Natural Range Materials Using Radiocarbon and Isotope Ratio Mass Spectrometry Analysis", incorporated herein by reference in its entirety. This test method measures the $^{14}C/^{12}C$ isotope ratio in a sample and compares it to the $^{14}C/^{12}C$ isotope ratio in a standard 100% bio-based material to give percent biobased content of the sample.

"Renewable" or "bio-based" compounds can be prepared from biomass using thermochemical methods (e.g., Fischer-Tropsch catalysts), biocatalysts (e.g., fermentation), or other processes, for example as described herein.

Preparation of Isobutene from Renewable Sources The present invention provides a simple process for obtaining high purity isobutene from a renewable hydrocarbon source. In one embodiment of the method of preparing renewable isobutene, an olefin mixture comprising isobutene and one or more linear butenes is obtained from a renewable hydrocarbon source and contacted (in liquid or gas state) with an adsorbent microporous material which selectively adsorbs the linear butenes thereby providing pure isobutene.

Separation of isobutene from the linear components requires an adsorbent having a pore size, which based on the critical diameter of the butenes, preferentially adsorbs linear butenes (i.e., 1-butene, trans-2-butene and cis-2-butene) while excluding isobutene. Suitable microporous adsorbent has a nominal pore size between 5 to 5.4 Å. In one embodiment, the nominal pore size of adsorbent is 5 Å.

In one embodiment, the olefin mixture is obtained from an alcohol mixture.

Figure 1:
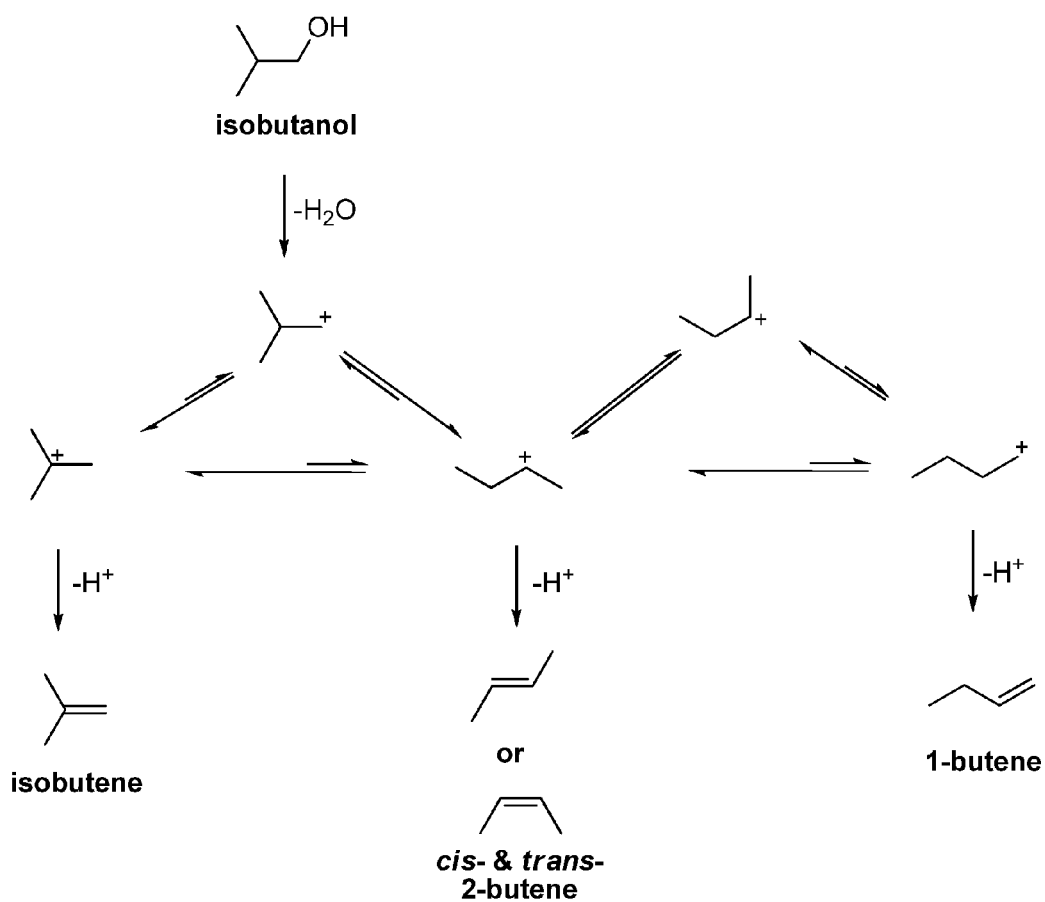
FIG. 1 illustrates the reaction pathway for the dehydration of isobutanol to produce butenes.

In one embodiment of the method of the present invention, an alcohol mixture comprising one or more butanols is first obtained from a renewable hydrocarbon source, which is subjected to dehydration conditions to form the olefin mixture as shown in FIG. 1, which is then contacted with the adsorbent microporous material to obtain the high purity renewable isobutene.

In one embodiment, the alcohol mixture comprises isobutanol. The renewable alcohol mixture comprising isobutanol can be prepared by any method known in the art, including as described in U.S. Publication No. 2010/0216958, incorporated herein by reference.

In one embodiment, the alcohol mixture comprising isobutanol can be derived from a fermented corn biomass.

In one embodiment, the olefin mixture is contacted with the microporous material for about 1 to about 24 hours. In one embodiment, the olefin mixture is contacted with the microporous material for about 6 to about 24 hours. In one embodiment, the olefin mixture is contacted with the microporous material for about 24 hours.

In one embodiment, the adsorbent microporous material useful in the present method comprises alkali metal aluminosilicate, for example aluminium oxide-silicate. In one embodiment the aluminium oxide-silicate has the formula $M_x[(AlO_2)_x(SiO_2)_y]\cdot zH_2O$ where M=Ca, Na, particularly, has the formula $Ca_{4,5}Na_3[(AlO_2)_{12}(SiO_2)_{12}] \cdot XH_2O$. The microporous material can be in the form of powder or pellets. In one embodiment the microporous material is in the form of molecular sieves.

In one embodiment, the adsorbent microporous material has a pH below 11, as measured by aqueous slurry. In one embodiment, the pH of the microporous material is above 8, as measured by aqueous slurry. In one embodiment, the pH of the adsorbent microporous material is between about 8 and about 11, as measured by aqueous slurry.

The term "high purity" used herein context with isobutene denotes that the isobutene is at least about 99.2% pure. In one embodiment, the isobutene obtained via the process of the present invention is at least 99.8% pure. In one embodiment, isobutene is at least about 99.99% pure.

Preparation of Polymers of Renewable Isobutene The renewable high purity isobutene of the present invention can be polymerized into useful polymers, including synthetic rubber, utilizing the same techniques that are applicable to isobutene that is derived from petrochemical sources. In one embodiment, the present invention is directed to a method of preparing a renewable polymer comprising polyisobutene, which comprises obtaining an olefin mixture comprising isobutene and one or more linear butenes from a renewable hydrocarbon source, contacting the olefin mixture with an adsorbent microporous material having an effective pore opening of 5 Å to 5.4 Å (wherein the linear butenes are selectively adsorbed to the microporous material), isolating the isobutene from contact with the microporous material, and polymerizing the renewable isobutene to obtain the renewable polymer.

The polymerization and recovery of renewable isobutene containing polymers are carried out according to various methods suitable for such monomer polymerization processes. This includes batch wise, semi-continuous, or continuous operations under conditions that exclude air and other atmospheric impurities, particularly oxygen and moisture. The polymerization of the isobutene monomer may also be carried out in a number of different polymerization reactor systems, including but not limited to bulk polymerization, vapor phase polymerization, solution polymerization, suspension polymerization, emulsion polymerization, and precipitation polymerization systems.

The polymerization reaction can be initiated using a vast array of different polymerization initiators or catalyst systems. The initiator or catalyst system used will be dependent upon the desired characteristics of the isobutene containing polymer being synthesized. For instance, isobutene containing polymers can be made using a free radical initiator, a redox initiator, or a cationic initiator. The preferred initiation or catalyst system will depend upon the polymer microstructure, molecular weight, molecular weight distribution, and chain branching desired. The preferred initiators will also depend upon whether the isobutene is being homopolymerized or copolymerized with additional monomers. In the case of copolymers, the initiator used will also depend upon whether it is desirable for the polymer being made to have a random, non-random, or tapered distribution of repeat units that are derived of the particular monomers.

The polymerization of isobutene may also be carried out in a suitable organic solvent that is liquid under the conditions of reaction and which is relatively inert. Some representative examples of suitable organic solvents include alkanes such as pentane, isooctane, cyclohexane, methylcyclohexane, isohexane, n-heptane, n-octane, n-hexane, and haloalkanes such as methyl chloride and chloroform.

The polymerization is typically carried out to attain a high conversion of monomers into polymer. Incremental monomer addition, or a chain transfer agent, may be used in order to avoid excessive gel formation. Such minor modifications are within the knowledge of a worker skilled in the relevant art. After the polymerization is complete, the polymer is recovered from a slurry or solution of the polymer. A simple filtration may be adequate to separate polymer from diluent. Other means for separating polymer from diluent may be employed. The polymer may be treated, separately or while slurried in the reaction mixture, in order to separate residues. Such a treatment may be with alcohols such as methanol, ethanol, or isopropanol, with acidified alcohols, or with other similar polar liquids. In many cases the polymers are obtained in hydrocarbon solutions and the polymer can be recovered by coagulation with acidified alcohol, e.g., rapidly stirred methanol or isopropanol containing 2% hydrochloric acid. Following this initial coagulation, the polymers may be washed with an appropriate liquid, such as methanol.

The isobutene can also be copolymerized with one or more additional comonomers to make useful copolymers. Some adjustments in the polymerization recipe or reaction conditions may be necessary to obtain a satisfactory rate of polymer formation, depending on the relative amount of isobutene included and the other monomers involved. Examples of comonomers that are useful in the practice of this invention include diene monomers, such as 1,3-butadiene, hexadienes, isoprene etc. Vinyl monomers can also be copolymerizable with isobutene to make useful polymers. Such vinyl monomers include styrene, [alpha]-methylstyrene, divinyl benzene, vinyl chloride, vinyl acetate, vinylidene chloride, methyl methacrylate, ethyl acrylate, vinylpyridine, acrylonitrile, methacrylonitrile, methacrylic acid, itaconic acid and acrylic acid. Mixtures of different comonomers can also be employed at differing levels.

The polymerization can be carried out in a polymerization reactor or a series of polymerization reactors. The polymerization zone will normally provide agitation to keep the monomers, polymer, initiator, and modifier well dispersed throughout the organic solvent the polymerization zone. Such continuous polymerizations are typically conducted in a multiple reactor system. The rubbery polymer synthesized is continuously withdrawn from the polymerization zone.

In one embodiment the renewable isobutene of the present invention is co-polymerized with isoprene under cationic polymerization conditions, wherein conventional polymerization procedure using any conventional diluents/solvent can be used. In one embodiment, the polymerization solvent comprises methyl chloride, chloroform, hexane or any other solvent as discussed above.

The polymerization reaction can be initiated using a strong protonic acid or a Lewis acid as the cationogenic initiator. In one embodiment, the Lewis acid can be used in combination with $H_2O$, one or more alcohols, one or more protic acids, and other $H^+$ sources known in the art.

Non limiting examples of protonic acid are $HCl$, $H_2SO_4$, $HNO_3$, $CF_3SO_3H$, $H_3PO_4$, and $HClO_4$. Non limiting examples of Lewis acid are $BF_3$, $BCl_3$, $AlCl_3$ and $SbF_5$.

In one embodiment, $AlCl_3/H_2O$ is used as cationogenic initiator. In one embodiment the initiator comprises a Friedel-Crafts catalyst capable of initiating cationic polymerization with an activator known in the art.

The cationogenic initiator can be soluble in the polymerization diluents/solvent and may be provided by itself or dissolved in a catalyst solvent. In this case, the catalyst solvent and polymerization diluent can be miscible in one another. The catalyst solvent may comprise methyl chloride, chloroform or hexane. In one embodiment, the catalyst solvent is the same as the polymerization diluent.

In one embodiment, a suitable cationogenic initiator is dissolved in a catalyst solvent is a solution of aluminum chloride ($AlCl_3$) in methyl chloride. The cationogenic initiator may be activated by a suitable proton source, such as water or hydrochloric acid (HCl).

Key to the present invention is to produce renewable isobutene-based polymers of sufficient molecular weight. The polymerization conditions may be modified to vary the molecular weight. In an embodiment of the invention, the isobutene based polymer has molecular weight ($M_w$) between 100 to 2000 kg/mol. In one embodiment, the molecular weight ($M_w$) of the isobutene based polymer is between 300 to 800 kg/mol. In one embodiment, the molecular weight ($M_w$) of the isobutene based polymer is between 400 to 600 kg/mol.

In one embodiment, the isobutene based polymer of the present invention comprises polydispersity ($M_w/M_n$) of 1.5 to 6.

The isobutene-based polymers of the present invention are not intended to be restricted to any one isobutene-based polymer or copolymer. By varying the monomer feed in the polymerization reaction, the isobutene-based polymer may be a homopolymer of polyisobutene, or a copolymer or terpolymer with any cationically polymerizable monomer(s).

Verification of Biobased Content All types of polymers made with the isobutene of this invention are verifiable as being made with isobutene that did not originate from a petrochemical source. Additionally, the isobutene containing polymers of this invention can also be distinguished from isobutene containing polymers that come from natural sources, such as natural rubber. Accordingly, the isobutene containing polymers of this invention are analytically verifiable as coming from the bio-renewable, environmentally friendly sources.

Assessment of the renewably based carbon content of a material can be performed through standard test methods, e.g. using radiocarbon and isotope ratio mass spectrometry analysis. ASTM International (formally known as the American Society for Testing and Materials) has established a standard method for assessing the biobased content of materials. The ASTM method is designated ASTM-D6866.

The application of ASTM-D6866 to derive "biobased content" is built on the same concepts as radiocarbon dating, but without use of the age equations. The analysis is performed by deriving a ratio of the amount of radiocarbon ($^{14}C$) in an unknown sample compared to that of a modern reference standard. This ratio is reported as a percentage with the units "pMC" (percent modern carbon). If the material being analyzed is a mixture of present day radiocarbon and fossil carbon (containing very low levels of radiocarbon), then the pMC value obtained correlates directly to the amount of biomass material present in the sample.

"Biobased materials" are organic materials in which the carbon comes from recently (on a human time scale) fixated $CO_2$ present in the atmosphere using sunlight energy (photosynthesis). On land, this $CO_2$ is captured or fixated by plant life (e.g., agricultural crops or forestry materials). In the oceans, the $CO_2$ is captured or fixated by photosynthesizing bacteria or phytoplankton. For example, a biobased material has a $^{14}C/^{12}C$ isotope ratio greater than 0. Contrarily, a fossil-based material, has a $^{14}C/^{12}C$ isotope ratio of about 0.

A small amount of the carbon atoms of the carbon dioxide in the atmosphere is the radioactive isotope $^{14}C$, which is created when atmospheric nitrogen is struck by a cosmic ray generated neutron, causing the nitrogen to lose a proton and form carbon of atomic mass 14 ($^{14}C$), which is then immediately oxidized to carbon dioxide. A small but measurable fraction of atmospheric carbon is present in the form of $^{14}CO_2$. Atmospheric carbon dioxide is processed by green plants to make organic molecules during the process known as photosynthesis. Virtually all forms of life on Earth depend on this green plant production of organic molecules to produce the chemical energy that facilitates growth and reproduction. Therefore, the $^{14}C$ that forms in the atmosphere eventually becomes part of all life forms and their biological products, enriching biomass and organisms which feed on biomass with $^{14}C$. In contrast, carbon from fossil fuels does not have the signature $^{14}C:^{12}C$ ratio of renewable organic molecules derived from atmospheric carbon dioxide.

To achieve a desired biobased content in an isobutene-based polymer, the mixture ratio of biobased isobutene to petroleum based isobutene in the polymer may be varied. In one embodiment, the biobased content for the isobutene-based elastomer of the present invention is greater than 0%. In another embodiment, the biobased content for the isobutene-based elastomer is greater than 20%. In another embodiment, the biobased content for the isobutene-based elastomer is greater than 40%. In another embodiment, the biobased content for the isobutene-based elastomer is greater than 60%. In another embodiment, the biobased content for the isobutene-based elastomer is greater than 80%. In another embodiment, the biobased content for the isobutene-based elastomer is greater than 90%.

Alternatively or additionally, the multiolefin content of the final polymer can be modified by adjusting the multiolefin monomer feed for the polymerization reaction. For example, 4 mol% (petroleum-based isoprene, renewable isoprene or mixtures thereof) incorporation of isoprene into the final butyl polymer would result in a biobased content of between 5 to 95% (ASTM D6866). As another example, 0.9 mol % (petroleum-based isoprene, renewable isoprene or mixtures thereof) incorporation of isoprene into the final butyl polymer would result in a biobased content of between 1 to 99% (ASTM D6866). Polymerization of a butyl rubber polymer using biobased isoprene and bio-isobutene will yield a bio-butyl rubber with a bio-based content of 100% (ASTM D6866).

The present invention also relates to a method for verifying that a polymer having repeating units derived from isobutene contains isobutene that is obtained from a renewable non-petroleum derived hydrocarbon source. This method involves (a) determining the biobased content of the polymer; and (b) verifying that the polymer is from a renewable non-petroleum derived source if the biobased content (as described in ASTM D6866) of greater than 0%.

The verification method can be applied to homopolymers or copolymer of isobutene.

In one embodiment, the method relates to verifying if a block copolymer having repeating units derived from isobutene contains isobutene that is from a renewable, sustainable non-petroleum derived source which comprises: (a) determining the percent modern carbon of at least one polyisobutene block in the copolymer; and (b) verifying that the isobutene from the copolymer is from a renewable, sustainable non-petroleum derived source if polyisobutene block has a total biobased content (ASTM D6866-08) greater than 0%.

Selective Separation of Isobutene from a Butene Mixture The present invention also relates to a simple purification method for selective separation of isobutene from a butene mixture. The purification method involves contacting an olefin mixture comprising the isobutene and one or more butenes with an adsorbent microporous material having a pore size, which based on the critical diameter of the butenes, preferentially adsorbs linear butenes (i.e., 1-butene, trans-2-butene and cis-2-butene) while excluding isobutene. Suitable microporous adsorbent has a nominal pore size between 5 to 5.4 Å. In one embodiment, the nominal pore size of adsorbent is 5 Å. The purified isobutene can then be isolated from contact with the adsorbent microporous material. In one embodiment, the selective separation can be achieved by contacting the olefin mixture with the adsorbent microporous material for about 1 to about 24 hours. In one embodiment, the olefin mixture is contacted with the microporous material for about 1 to about 24 hours. In one embodiment, the olefin mixture is contacted with the microporous material for about 24 hours. The olefin mixture can be in liquid state or gas state. The olefin mixture can be derived from a renewable hydrocarbon source (as describe above) or a petrochemical source.

Figure 2:
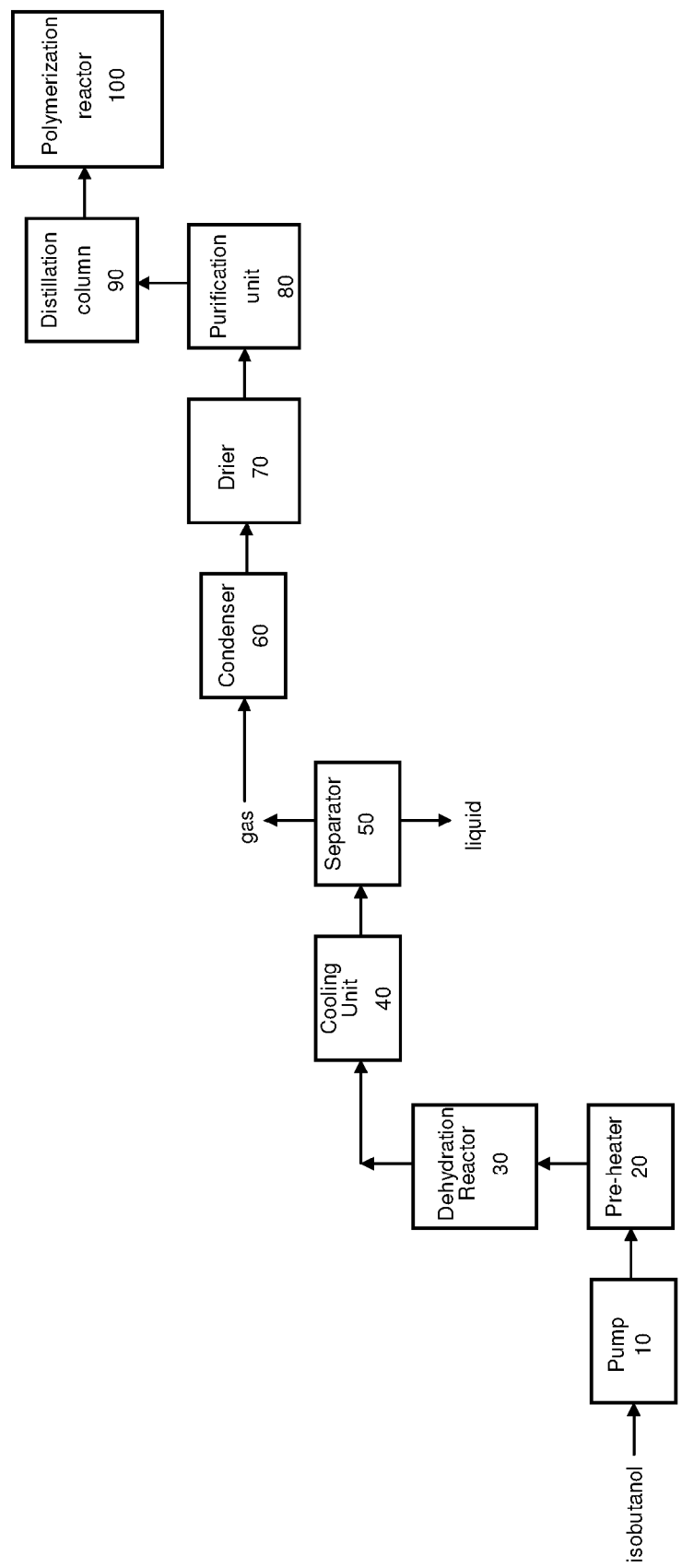
FIG. 2 illustrates the process of obtaining renewable isobutene and preparation of an isobutene based polymer.

FIG. 2 illustrates the schematic process of an embodiment of the present invention. According to FIG. 2, liquid alcohol mixture comprising one or more butanols is fed into the system using a pump 10. The isobutanol may be isobutanol derived from a petrochemical source or a fermentative source. The alcohol mixture is vaporized to gas in a preheater 20 at a temperature between 275° C. and 350° C., preferably at the same temperature as the dehydration reactor 30. The gas phase alcohols enter a dehydration reactor 30 containing a fixed bed dehydration catalyst at a temperature between 275° C. and 350° C., preferably at 325° C. The dehydration catalyst includes acids such as solid-supported acid catalyst and metal oxides such as alumina, titania, zirconia, silica-alumina and zeolites. Solid alumina catalysts are preferable from the viewpoint of catalyst life and isobutene selectivity. The dehydration reaction takes place in the dehydration reactor 30. The reaction product is cooled using a cooling unit 40 at a temperature between 1° C. to 5° C. A feed is provided to a separator 50 from the condenser 40. Gas and liquid products are separated by the separator 50. The liquid product is a mixture of water and isobutanol.

The ratio of water to isobutanol depends on the conversion efficiency of the dehydration reaction. Optionally, a recycle system may be utilized to recover the one or more butanols in the liquid phase. Some embodiments of the process include these optional recycle steps in order to achieve advantageous overall process economics. The separated gas products are a mixture of butenes (isobutene, 1-butene, cis-2-butene, trans-2-butene). The distribution of the gaseous butenes are significantly influenced by the experimental conditions (e.g., the amount of catalyst, flow rate, temperature, etc.). The gaseous mixture may be condensed to a liquid using conventional low temperature methods. According to one embodiment, the separated gaseous butenes are condensed to the liquid phase in a condenser 60 at a temperature between −10° C. and −40° C. The conversion of the butanol to butenes may be determined by measuring the flow of gas from the separator, using a flow-meter, and comparing against the theoretical flow at 100% conversion. To ensure high purity of isobutene, the liquid butenes may be distilled by conventional means to remove any residual $C_5$ and greater hydrocarbons.

The condensed butenes are dried using a drying agent. The residence time of the liquid butene with the drying agent in the drier 70 is about 24 hours. The drying agent may be any suitable drying agent. In one embodiment, the drying agent is a 3 Å molecular sieve activated by heating to at least 120° C. in a vacuum oven for about 24 hours prior to use.

Isobutene from the dried butene mixture is separated from the linear components using a microporous adsorbent in a purification unit 80. As discussed above, separation of isobutene from the linear components requires an adsorbent having a pore size, which based on the critical diameter of the butenes, preferentially adsorbs 1-butene, trans-2-butene and cis-2-butene while excluding isobutene. A polymerization reactor 100 is provided for the polymerization of isobutene-based polymers using the purified isobutene.

Oligomarization of Isolkenes The present invention also relates to a simple and energy efficient process of oligomerizing isoalkenes to prepare diiso- and/or triisoalkenes.

It has been found unexpectedly that porous adsorbent material can catalyze the oligomerization of alkenes. The present invention has established that the oligomers of isoalkenes, such as isobutene can be easily formed by contacting an olefin mixture with a suitable porous adsorbent material under condition which suitable for oligomerization reaction.

Suitable microporous adsorbent for the oligomerization process of the present invention can have a nominal pore size about 3 to about 10 Å. In one embodiment, the nominal pore size of adsorbent porous material is about 5 to 5.4 Å. In one embodiment, the nominal pore size of adsorbent porous material is about 5 Å.

In one embodiment the adsorbent microporous material useful in the present method comprises alkali metal aluminosilicate, for example aluminium oxide-silicate. In one embodiment, the aluminium oxide-silicate has the formula $M_x[(AlO_2)_x(SiO_2)_y]\cdot\theta zH_2O$ where M=Ca, Na, particularly, has the formula $Ca_{4.5}Na_3[(AlO_2)_{12}(SiO_2)_{12}]\cdot XH_2O$. The adsorbent microporous material can be in the form of powder or pellets. In one embodiment, the adsorbent microporous material is in the form of molecular sieves.

The oligomerization can be achieved at a temperature from about 15° C. to about 250° C. In one embodiment the oligomerization can be achieved at room temperature. In one embodiment the reaction temperature for the oligomerization process is about 22° C.

In one embodiment, the olefin mixture is contacted with the adsorbent microporous material for about 24 hours or more at room temperature to achieve the oligomarization. In one embodiment reaction time at room temperature is about 48 hours or more. The oligomerization process can be completed in a shorter period of time by heating the reaction mixture up to about 250° C.

In one embodiment, the pH of the adsorbent microporous material is between about 8 and about 11, as measured by aqueous slurry.

The invention will now be described with reference to specific examples. It will be understood that the following examples are intended to describe embodiments of the invention and are not intended to limit the invention in any way.

$^1$H NMR data was obtained using a Bruker DRX 500 MHz spectrometer (500.13 MHz) in $CDCl_3$ with the residual $CHCl_3$ peak used as an internal reference. GC/MS data was collected on a Hewlett Packard HP 6890 Series GC System equipped with a Hewlett Packard 5973 Mass Selective Detector. GPC data was measured on a Waters GPC (SEC) instrument using six Ultrastyragel columns (100, 500, $10^3$, $10^4$, $10^5$ and $10^6$ Å) heated to 35° C. with a DRI 410 detector. The mobile phase was THF with a constant flow rate of 1 mL/min The instrument was calibrated using narrow MWD polystyrene standards and toluene was used as an internal reference. Molecular weights were calculated using EMPOWER GPC software.

EXAMPLE 1

Figure 3:
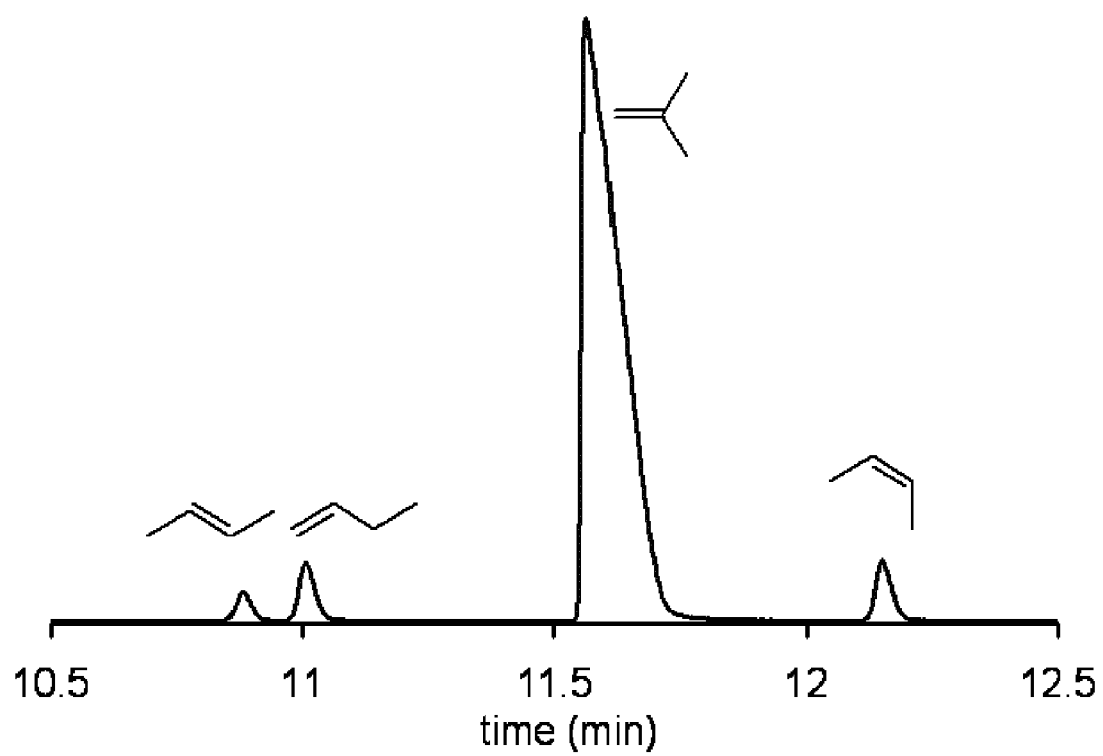
FIG. 3 illustrates the GC/MS trace following the dehydration of bio-isobutanol (supplied by GEVO, typical composition: 94% isobutene and 6% linear butenes: 1-butene, cis-and trans-2-butene)

Dehydration
Isobutanol source: fermented corn biomass
Reactor type: Fixed bed
catalyst: 10 g BASF (AL3996R)
Temperature: 325° C.
Pressure: 1 bar
Isobutanol flow rate: 1 mL/min
GHSV: 4.8 h$^{-1}$ The dehydration catalyst was received from BASF (AL3996R) in 3.5 mm ring form. The rings were crushed using a mortar and pestle and passed through a series of sieves. The catalyst used was collected from 1.0 mm sieve. The isobutanol was vaporized to gas in a preheater at 325° C. prior to entering a stainless steel tubular reactor (⅜" ID, 16" length) packed with the BASF A13996R supported by glass beads. The temperature of the reactor was 325° C. Gas and liquid products were separated using a knock-out pot. The separated gaseous butenes were condensed in a 500 ml Schlenk flask, containing 30g of Type 3 Å molecular sieves, immersed in an ethanol/liq.$N_2$ bath. The gaseous butenes were analyzed using GC/MS (FIG. 3). The gas composition of the gas product from the dehydration process was 95% isobutene, 1% 1-butene, 2% cis-2-butene, 1% trans-2-butene and 1% others. The conversion of the butanol to butenes tubes was measured using a soap film flow-meter. At 325° C., the conversion rate was greater than 98%.

Drying
The gaseous butenes mixture from the dehydration process, collected by condensing the gas to a liquid in a 500 mL Schlenk flask containing 30 grams of 3 Å molecular sieve, was allowed to dry over the 3 Å molecular sieves (Aldrich) for about 24 hours at room temperature. Prior to the drying of the butenes, the molecular sieve was activated by heating the molecular sieve at a temperature of 120° C. in a vacuum oven for about 24 hours prior to use.

Figure 4:
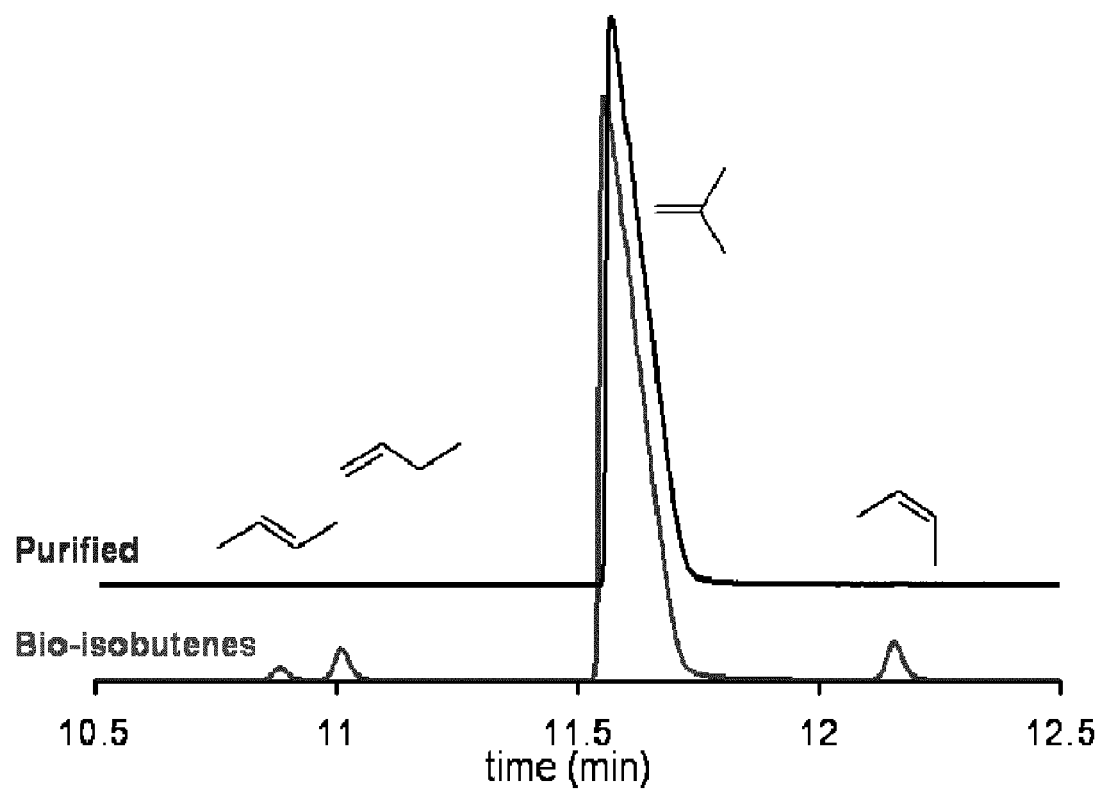
FIG. 4 illustrates the GC/MS trace before (bottom) and after (top) treatment with 5 Å UOP molecular sieves to remove linear butenes.

Purification of Butene Mixture in Liquid State
The flask containing the condensed dried butene mixture was attached to a 500 mL Schlenk flask containing 40 g of Type 5 Å molecular sieve adsorbent (UOP), which was previously dried for 24 hrs at 120° C. in a vacuum oven. The Schlenk flask containing 5 Å molecular sieve adsorbent was cooled by immersing it into a Dewar containing liquid nitrogen. The Schlenk flask containing the butenes was kept warm by using a water bath (approximately 30° C.) and opened. The butenes were transferred to the 5 Å molecular sieve Schlenk flask immersed in a liquid nitrogen bath where they immediately condensed to the solid state. Once the transfer was complete the Schlenk flasks were closed and allowed to warm to room temperature. The condensed liquid butenes remained in contact with the 5 Å molecular sieve adsorbent for about 24 hours. At this point, the purified isobutene was transferred to an empty storage flask for cold distillation at between −6° C. to remove any residual $C_5$ and greater hydrocarbons. The removal of linear butenes was monitored by GC/MS. The GC/MS trace in FIG. 4 shows the removal of the linear butenes in the purified sample.

Purification of Butene Mixture in Gaseous State

The butenes were transferred to a 2 mL air tight vial containing 15 mg 5 Å molecular sieve. The gaseous butenes remained in contact with the 5 Å molecular sieve adsorbent for up to 24 hours. The removal of linear butenes by the molecular sieves was monitored by GC/MS as shown in table 1.

TABLE 1

| Elapsed Time (hrs) | trans-2-butene | 1-butene | isobutene | cis-2-butene |
|---|---|---|---|---|
| 0 | 2.237 | 1.461 | 93.784 | 2.518 |
| 1 | 0 | 0 | 97.783 | 2.217 |
| 2 | 0 | 0 | 98.226 | 1.657 |
| 3 | 0 | 0 | 98.441 | 1.441 |
| 4 | 0 | 0 | 98.603 | 1.271 |
| 5 | 0 | 0 | 98.815 | 1.099 |
| 6 | 0 | 0 | 98.796 | 1.028 |
| 22 | 0 | 0 | 100 | 0 |

Polymerization
Isobutene: 20 ml
Isoprene: 0.6 ml
Solvent: 180 ml MeCl
Catalyst: 0.3 g $AlCl_3$ was dissolved in 100 mL MeCl at −30° C.

Batch slurry polymerization reactions were carried out in an MBRAUN glove box under a dry $N_2$ atmosphere. Oxygen and moisture levels were maintained below 20 ppm. Standard recipes were used for all experiments and are as follows: A 500 mL flask was prechilled in a heptane bath at −95° C. To this was added 0.6 mL of isoprene, 20 mL isobutene and 180 mL of methyl chloride (MeCl). The resulting solution was stirred using an overhead stirrer until a solution temperature of −94° C. was reached. To this was added 3 mL of an $AlCl_3$/MeCl catalyst solution (0.3 g $AlCl_3$ was dissolved in 100 mL MeCl at −30° C.). The resulting slurry was stirred for an additional 5 min. before 1 mL of stopper solution (2.5 g sodium hydroxide in 200 mL of ethanol) was added to terminate the polymerization. Hexanes (~200 mL) was added to the reaction mixture along with Irganox 1010, an antioxidant, and allowed to sit at room temperature for about 24 hours to fully remove the methyl chloride. The polymer solution was coagulated by the addition of excess ethanol. The butyl rubber was collected and dried in a vacuum oven at 60° C. about for about 24 hours.

EXAMPLE 2

The experimental procedure of Example 1 was repeated using a petroleum based isobutene supplied by LANXESS Inc. in Sarnia, Ontario, Canada.

The cationic polymerization of renewable isobutene with isoprene to produce butyl rubber was successfully demonstrated. The butyl rubber polymers were characterized by $^1$H NMR and GPC (Table 2). The biobased content was verified using the methodology described in ASTM D6866-08.

TABLE 2

| Exp | Conversion | Mn | Mw | Mz | PDI | % unsats ($^1$H NMR) | Biobased content (ASTM D6866-08) |
|---|---|---|---|---|---|---|---|
| 1 | 83% | 188581 | 504416 | 984274 | 2.7 | 1.5 | 99% |
| 2 | 86% | 174579 | 494670 | 982223 | 2.8 | 1.5 | 0% |

The molecular weight $M_w$ of the biobased butyl rubber is comparable to the control sample.

EXAMPLE 3

Figure 5:
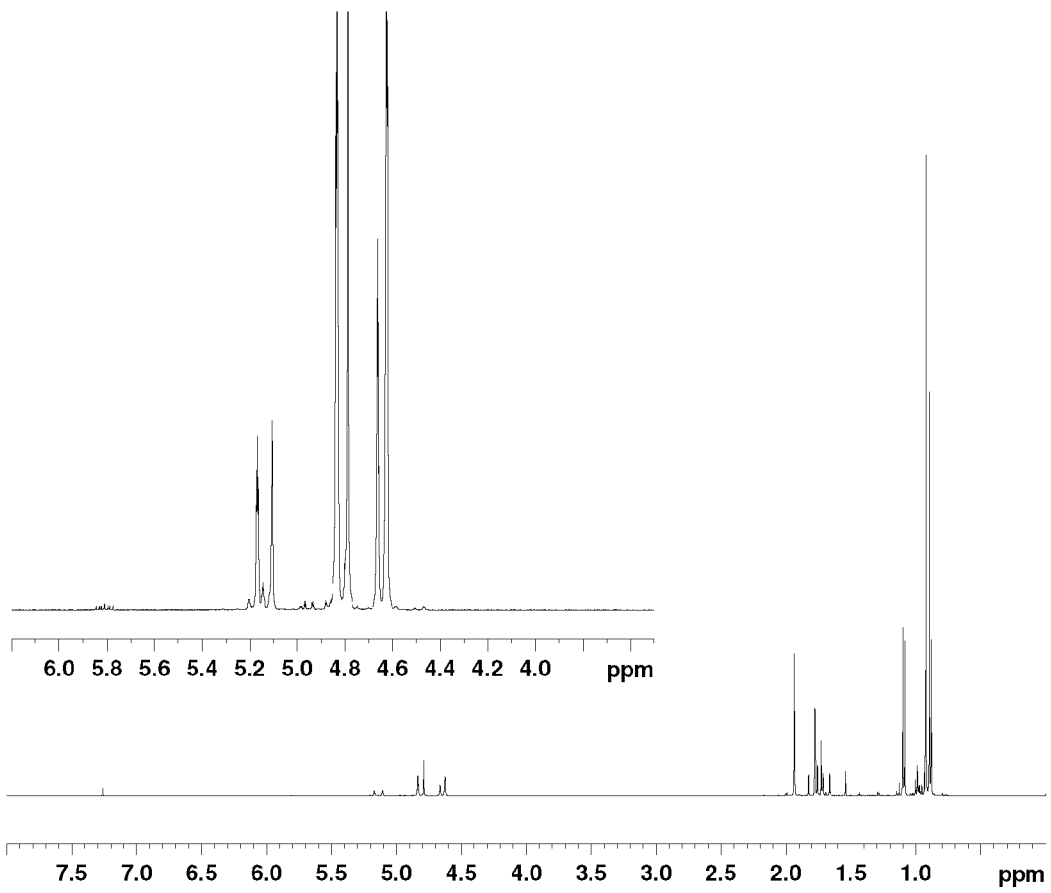
FIG. 5 illustrates the $^1$H NMR trace of the oligomerization of the purified isobutene.

Condensed liquid butenes obtained in Example 1 were allowed to remain in contact with the 5 Å molecular sieve adsorbent for about 48 hours. The presence of isobutene oligomers was confirmed by $^1$H NMR (FIG. 5). Quantitative oligomerization of pure liquid isobutene over 5 Å molecular sieves was demonstrated at room temperature for purification times greater than 48 hours. Oligomeric butenes that were produced were predominately diisobutenes and diisobutenes.

All documents cited in the Detailed Description of the invention are, in relevant part, incorporated herein by reference; the citation of any document is not to be construed as an admission that it is prior art with respect to the present invention.

It is obvious that the foregoing embodiments of the invention are examples and can be varied in many ways. Such present or future variations are not to be regarded as a departure from the spirit and scope of the invention, and all such modifications as would be obvious to one skilled in the art are intended to be included within the scope of the following claims.

We claim:

1. A method of preparing polyisobutene polymer from a renewable hydrocarbon source, the method comprising:
    obtaining an alcohol mixture comprising one or more butanols from the renewable hydrocarbon source; and
    contacting the alcohol mixture with a dehydration catalyst to form an olefin mixture comprising one or more linear butenes and isobutene;
    contacting the olefin mixture with an adsorbent microporous material having an effective pore opening of 5Å to 5.4Å for about 6 to about 24 hours in an enclosed container to selective adsorb the linear butenes to the microporous material;
    isolating the isobutene from the micro porous a material and adsorbed linear butenes; and
    polymerizing the isobutene to obtain the polyisobutene polymer.

2. A method of preparing polyisobutene polymer from a renewable source, the method comprising:
    a) obtaining an olefin mixture comprising isobutene and one or more linear butenes from a renewable hydrocarbon source;
    b) contacting the olefin mixture with an adsorbent microporous material having an effective pore opening of 5Å to 5.4Å for about 6 to about 24 hours in an enclosed container to selectively adsorb the linear butenes to the microporous material;
    c) isolating the isobutene from the microporous material and adsorbed linear butenes; and
    d) polymerizing the isobutene in the presence of an additional monomer to obtain a co-polymer of isobutene as the polyisobutene polymer.

3. The method of claim 2, wherein the co-polymer is butyl rubber.

4. The method of claim 2, wherein the polymerization is carried out under cationic polymerization conditions.

5. The method of claim 2, wherein the olefin mixture is contacted with the microporous material at room temperature, without pre-treatment of the microporous material.

6. The method of claim 5, wherein the microporous material comprises aluminium oxide-silicate.

7. The method of claim 5, wherein the olefin mixture is in a liquid state.

8. The method of claim 5, wherein the olefin mixture is in a gas state.

9. A method of preparing high purity renewable isobutene, the method comprising:
   obtaining an alcohol mixture comprising one or more butanols from a renewable hydrocarbon source;
   contacting the alcohol mixture with a dehydration catalyst to form an olefin mixture comprising one or more linear butenes and isobutane;
   contacting the olefin mixture with an adsorbent microporous material having an effective pore opening of 5Å to 5.4Å for about 6 to about 24 hours in an enclosed container to selectively adsorb the linear butenes to the microporous material; and
   isolating the renewable isobutene from contact with the microporous material and adsorbed linear butenes.

10. The method of claim 9, further comprising producing the alcohol mixture containing the one or more butanols by fermentation of corn biomass.

11. The method of claim 9, wherein contacting the olefin mixture with the microporous material comprises:
    placing the microporous material and the olefin mixture in a container; and
    contacting the olefin mixture and microporous material at ambient temperature for about 6 to about 24 hours.

12. The method of claim 11, wherein the microporous material comprises aluminium oxide-silicate.

13. The method of claim 11, wherein the olefin mixture is in a liquid state.

14. The method of claim 11, wherein the olefin mixture is in a gas state.

* * * * *